US012784899B2

(12) United States Patent
Caudill et al.

(10) Patent No.: US 12,784,899 B2
(45) Date of Patent: Nov. 3, 2026

(54) MACHINE LEARNING MODEL TO EVALUATE HEALTHCARE FACILITIES

(71) Applicant: MatrixCare, Inc., Bloomington, MN (US)

(72) Inventors: Joseph Martin Caudill, Birmingham, AL (US); Danny Wong, Jonestown, TX (US); Bradley Steven Hall, Pelham, AL (US)

(73) Assignee: MatrixCare, Inc., Bloomington, MN (US)

( * ) Notice: Subject to any disclaimer, the term of this patent is extended or adjusted under 35 U.S.C. 154(b) by 460 days.

(21) Appl. No.: 17/650,563

(22) Filed: Feb. 10, 2022

(65) Prior Publication Data

US 2023/0253100 A1 Aug. 10, 2023

(51) Int. Cl.

| | |
|---|---|
| ***G16H 40/20*** | (2018.01) |
| ***G06N 20/00*** | (2019.01) |
| ***G16H 10/60*** | (2018.01) |
| ***G16H 50/20*** | (2018.01) |

(52) U.S. Cl.

CPC ............. *G16H 40/20* (2018.01); *G06N 20/00* (2019.01); *G16H 10/60* (2018.01); *G16H 50/20* (2018.01)

(58) Field of Classification Search

None

See application file for complete search history.

(56) References Cited

U.S. PATENT DOCUMENTS

| | | | | |
|---|---|---|---|---|
| 2008/0172251 | A1* | 7/2008 | Reichert | G06Q 10/10 705/2 |
| 2008/0215363 | A1* | 9/2008 | Kasprisin | G16H 40/20 705/2 |
| 2012/0173277 | A1* | 7/2012 | Yates | G06Q 10/063114 705/2 |
| 2013/0311197 | A1* | 11/2013 | Hummer | G06Q 30/0283 705/2 |
| 2015/0106123 | A1* | 4/2015 | Amarasingham | G16H 10/60 705/3 |
| 2016/0092641 | A1* | 3/2016 | Delaney | G16H 40/20 705/3 |
| 2018/0174121 | A1* | 6/2018 | Denton | G06Q 20/12 |
| 2019/0304582 | A1* | 10/2019 | Blumenthal | G16H 40/67 |
| 2019/0385711 | A1* | 12/2019 | Shriberg | G16H 15/00 |
| 2020/0211701 | A1* | 7/2020 | Martindale | G16H 10/60 |
| 2020/0285804 | A1* | 9/2020 | Rubin | G06F 40/169 |

* cited by examiner

*Primary Examiner* — John P Go

(74) *Attorney, Agent, or Firm* — Patterson + Sheridan, LLP

(57) ABSTRACT

Embodiments herein describe a patient evaluation system that predicts a revenue stream corresponding to a patient if admitted into a healthcare facility. In one embodiment, the patient evaluation system parses medical records corresponding to a patient to automatically identify inputs into a daily rate calculator for determining a reimbursement or cost rate (e.g., a daily rate) corresponding to the patient. In addition to determining this rate, the patient evaluation system can use a ML model to estimate or predict the length of stay of the patient. Using the reimbursement or cost rate and the predicted length of stay, the patient evaluation system can estimate or predict the revenue stream corresponding to patient's stay at the healthcare facility. This information can be output in a graphical user interface which can be used to decide whether or not to recommend the patient be admitted to the healthcare facility.

18 Claims, 8 Drawing Sheets

MACHINE LEARNING MODEL TO EVALUATE HEALTHCARE FACILITIES

BACKGROUND

Field

Embodiments of the present disclosure relate to predicting revenue streams for a patient using a machine learning (ML) model.

Description of the Related Art

Patients often move between different healthcare facilities such as assisted living facilities, hospitals, surgery centers, skilled nursing centers, etc. An evaluator typically has to scan the patient's medical records, which can include many pages of documents, to determine whether a particular healthcare facility is suitable for the patient. For example, the evaluator may have to read the medical records to identify the patient's medical diagnosis, the medications the patient is prescribed, a responsible payer (e.g., private insurance or government payer), and special medical equipment needed by the patient and then determine whether the healthcare facility has the equipment, staff, and resources to satisfy the patient's needs.

In addition, the evaluator may enter the patient information into a cost calculator to determine the amount a payor (e.g., a government entity or a private insurance) will reimburse the facility. For example, in the United States, the Centers for Medicare & Medicaid Services (CMS) provides a Patient Driven Payment Model (PDPM) calculator that generates a daily rate that is paid to the healthcare facility (e.g., a skilled nursing facility) based on a patient's diagnosis and required medications. Searching the medical records to enter the required information into a payment calculator is a time consuming task. Further, current payment calculators provide a daily rate but do not indicate a total amount of revenue associated with the patient.

SUMMARY

One embodiment herein is a method that includes parsing, using one or more computer processors, a medical record for a patient to identify an input to a rate calculator, determining, using the rate calculator, a reimbursement or cost rate of the patient at a healthcare facility based on the identified input, predicting, using a machine learning (ML) model, a length of stay of the patient based on a diagnosis of the patient, and determining, before the patient is admitted into the healthcare facility, a revenue stream corresponding to the patient based on the reimbursement or cost rate and the predicted length of stay.

Another embodiment herein is a non-transitory computer readable medium comprising instructions to be executed in a processor, the instructions when executed in the processor perform an operation. The operation includes parsing a medical record for a patient to identify an input to a rate calculator, determining, using the rate calculator, a reimbursement or cost rate of the patient at a healthcare facility based on the identified input, predicting, using a machine learning (ML) model, a length of stay of the patient based on a diagnosis of the patient, and determining, before the patient is admitted into the healthcare facility, a revenue stream corresponding to the patient based on the reimbursement or cost rate and the predicted length of stay.

Another embodiment herein is a system that includes a processor and memory storing code which, when executed by the processor, performs an operation. The operation includes parsing a medical record for a patient to identify an input to a rate calculator, determining, using the rate calculator, a reimbursement or cost rate of the patient at a healthcare facility based on the identified input, predicting, using a machine learning (ML) model, a length of stay of the patient based on a diagnosis of the patient, and determining, before the patient is admitted into the healthcare facility, a revenue stream corresponding to the patient based on the reimbursement or cost rate and the predicted length of stay.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, may admit to other equally effective embodiments.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

Embodiments herein describe a patient evaluation system that predicts a revenue stream corresponding to a patient if admitted into a healthcare facility. In one embodiment, the patient evaluation system receives medical records corresponding to a patient (e.g., a Continuity of Care Document (CCD), an Electronic Health Record (EHR), patient notes, etc.). The system can use a keyword search or natural language processing to identify a medical diagnosis (or diagnoses) of the patient, the medications currently prescribed to the patient, responsible payer (e.g., private insurance or government payer), or special medical equipment or treatments needed by the patient (e.g., lifts or frequent computed tomography (CT) scans) which can be used as inputs into a daily rate calculator. This daily rate calculator can be calculator provided by a payor (e.g., a government healthcare payor or private insurance) that indicates the daily rate the payor pays for the patient if admitted into the facility. The system, rather than the evaluator, can parse the medical records to identify the input for the daily rate calculator which can save time and cut down on human errors.

In addition to determining the daily rate (e.g., the amount paid by the payor per day or the cost of treating the patient per day), the patient evaluation system can use a ML model to estimate or predict the length of stay of the patient. In one embodiment, the ML model receives the diagnosis (or diagnoses) of the patient as inputs and outputs a predicted length of stay for the patient at the facility. Using the daily rate and the predicted length of stay, the patient evaluation system can estimate or predict the revenue stream (or the total revenue) corresponding to patient's stay at the healthcare facility. This information can be output in a graphical user interface (GUI) to the evaluator which she can use to decide whether or not to recommend the patient be admitted (or transferred) to the healthcare facility.

In one embodiment, the ML model used to predict the length of stay is trained using medical records of patients previously admitted, and then discharged, from a healthcare facility (or from a plurality of healthcare facilities). For example, the patient evaluator system can collect medical records for previous patients who have been discharged from one or more healthcare facilities. The system can then parse the medical records to identify the patients' diagnoses and their length of stay at their respective healthcare facilities. This information can be formatted into training data that is used to train the ML model. Once trained, the ML model can then predict, based on the diagnosis (or diagnoses) of a current patient, her length of stay at the healthcare facility. Further, in addition to considering the patient's diagnosis, the ML model can be trained to predict the length of stay using additional factors such as age, weight, ethnicity, family medical history, and the like.

Figure 1:
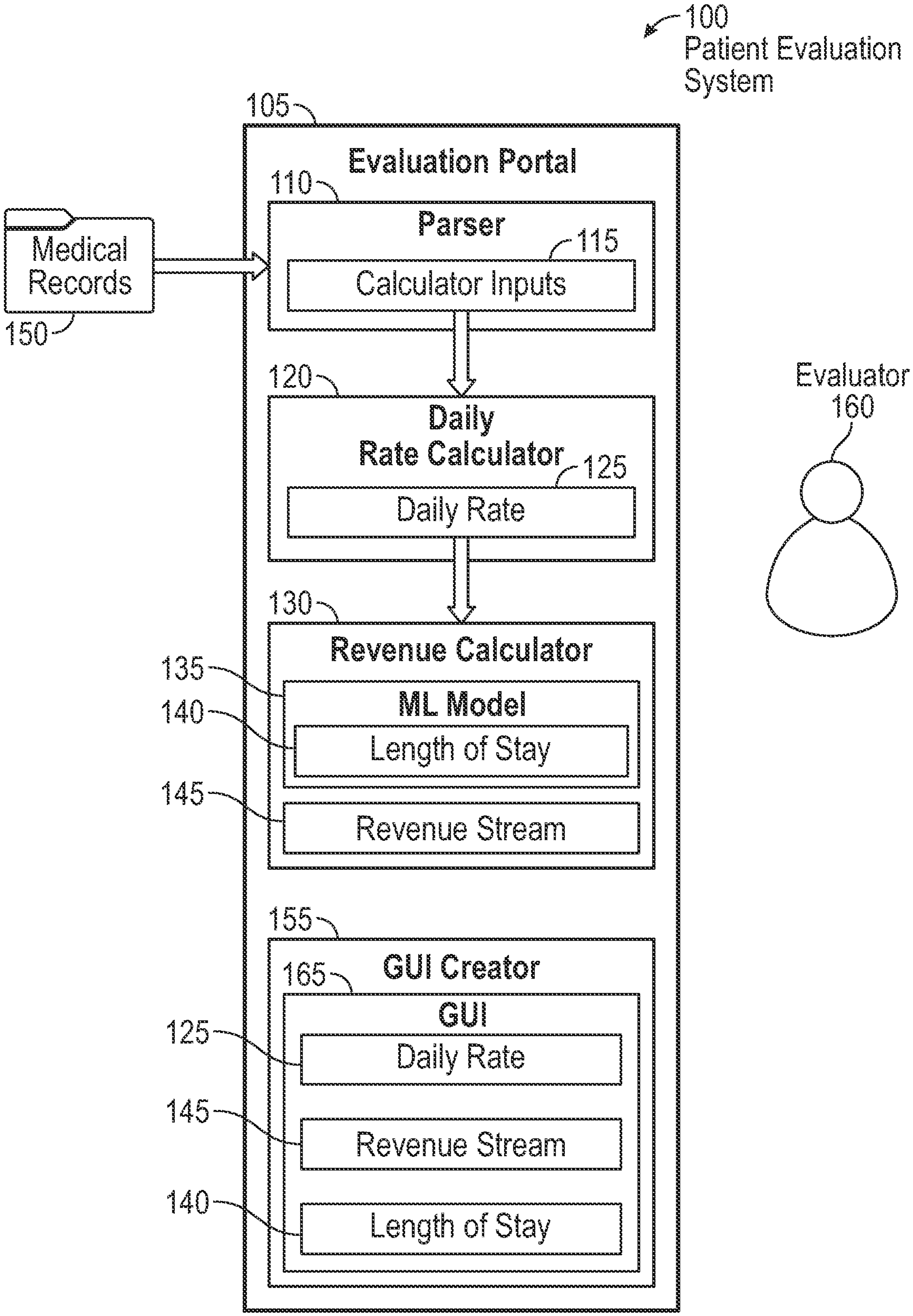
FIG. 1 illustrates a block diagram of a patient evaluation system for calculating a daily rate and a revenue stream for a patient, according to one embodiment.

FIG. 1 illustrates a block diagram of a patient evaluation system 100 for calculating a daily rate and a revenue stream for a patient, according to one embodiment. The patient evaluation system 100 includes a parser 110, a daily rate calculator 120, a revenue calculator 130, and a GUI creator 155. The parser 110 parses a patient's medical records 150 to identify calculator inputs 115 for the daily rate calculator 120. In one embodiment, an evaluator 160 transmits the medical records 150 (e.g., a CCD or EHR) to the evaluation portal 105 so that the portal 105 can provide a recommendation to the evaluator 160. The parser 110 can perform a keyword search or use natural language processing to identify medical information that can be used as the calculator inputs 115, such as medical diagnoses, prescriptions, insurance, special medical equipment needed by the patient, and the like. As part of the recommendation, the evaluation portal 160 can use these calculator inputs 115 to calculate a daily rate indicating the amount a particular healthcare facility is paid, per day, by the payor, as well as predict a total revenue stream generated from the patient's stay at the facility. While the embodiments below discuss calculating a daily rate, the rate may be based on a different time period just as a weekly rate or hourly rate. More generally, the rate determined by the calculator rate calculator 120 can be reimbursement or cost rate over any defined period of time.

The daily rate (or more generally, the reimbursement or cast rate) can help the evaluator 160 to determine whether or not to recommend the patient be admitted or transferred to a particular healthcare facility. For example, the evaluator 160 may be tasked with identifying the healthcare facility that is most compatible with the needs of the patient. Because the patient may be referred to the evaluation portal 105 by the evaluator 160, in the discussion below the patient can also be referred to as a referral.

While the embodiments herein discuss considering the financial costs and revenue corresponding to treating a patient at a particular healthcare facility, the evaluator portal 105 can consider other factors for determining whether the healthcare facility is a good fit for the patient. For example, the parser 110 may compare the medical diagnoses, prescriptions, insurance, and special medical equipment needed by the patient to attributes about a healthcare facility (or a pool of healthcare facilities). These attributes can indicate which ailments or diseases a healthcare facility can treat, which prescriptions the facility can administer, the medical equipment in the facility, the lab capabilities of the facility, the expertise of the staff at the facility, the insurance accepted at the facility, and the like. In one embodiment, the portal 105 compares the attributes of the facility to the information identified in the medical records 150 by the parser 110 to determine whether the facility can, e.g., treat the patient's illness, or whether that facility has a special lift needed by the patient. The evaluator portal 105 can provide this compatibility information to the evaluator 160 along with financial information such as the daily rate and the revenue stream.

In another embodiment, the medical records 150 may be provided to the evaluation portal 105 by the patient or a legal guardian. For example, the patient may be looking for an assisted living center, rehabilitation center, or skilled nursing center. The patient can rely on the portal 105 to evaluate a pool of candidate healthcare facilities and provide a recommendation indicating which would be the best fit for the patient in response to factors such as the patient's medical diagnosis, special needs, medications, budget, and payor (e.g., insurance).

In one embodiment, to identify the calculator inputs 115, the parser 110 may store a list of predefined inputs and then search the medical records 150 for a phrase or word that matches an input in the list (or is a derivative thereof). If the medical records 150 are not in a readable or editable form, the parser 110 may first perform an Optical Character Recognition (OCR) to, e.g., convert a PDF file or handwritten notes into a readable form.

As shown, the daily rate calculator 120 receives the calculator inputs 115 from the parser 110 and uses these inputs 115 to calculate a daily rate 125 for the patient at the facility. In some embodiments, the daily rate 125 may be different depending on which facility is being considered. For example, different payors (e.g., different government healthcare agencies/programs and private insurers) may pay different amounts for different healthcare facilities (e.g., a hospital versus a rehabilitation center versus a skilled nursing center). That is, the daily rate calculator 120 may use payor information to determine the daily rate 125, or the evaluator portal 105 may use a different daily rate calculator 120 depending on which healthcare facility is currently being evaluated.

Figure 3:
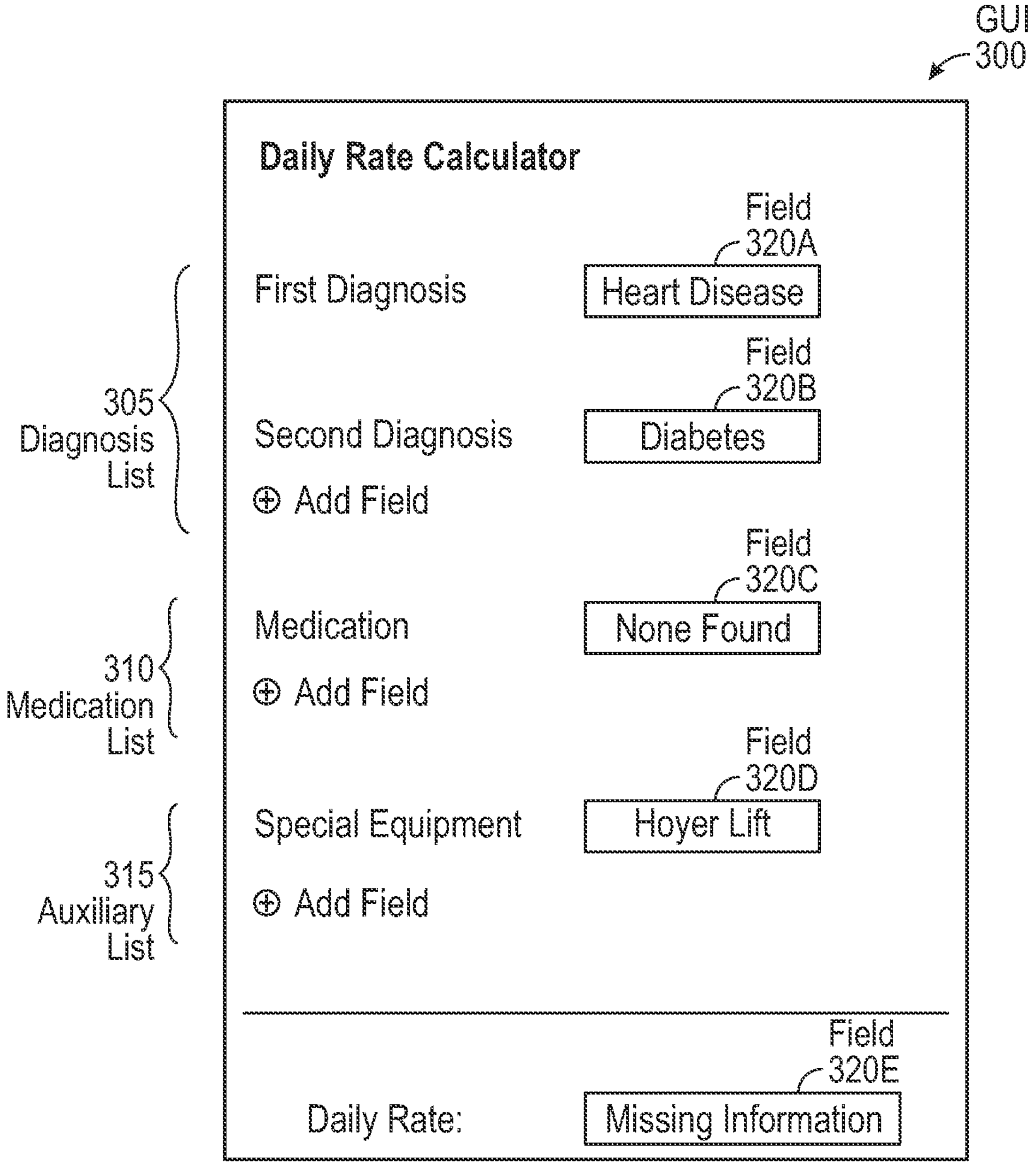
FIGS. 3 and 4 are graphical user interfaces displaying a daily rate calculator, according to one embodiment.
Figure 4:
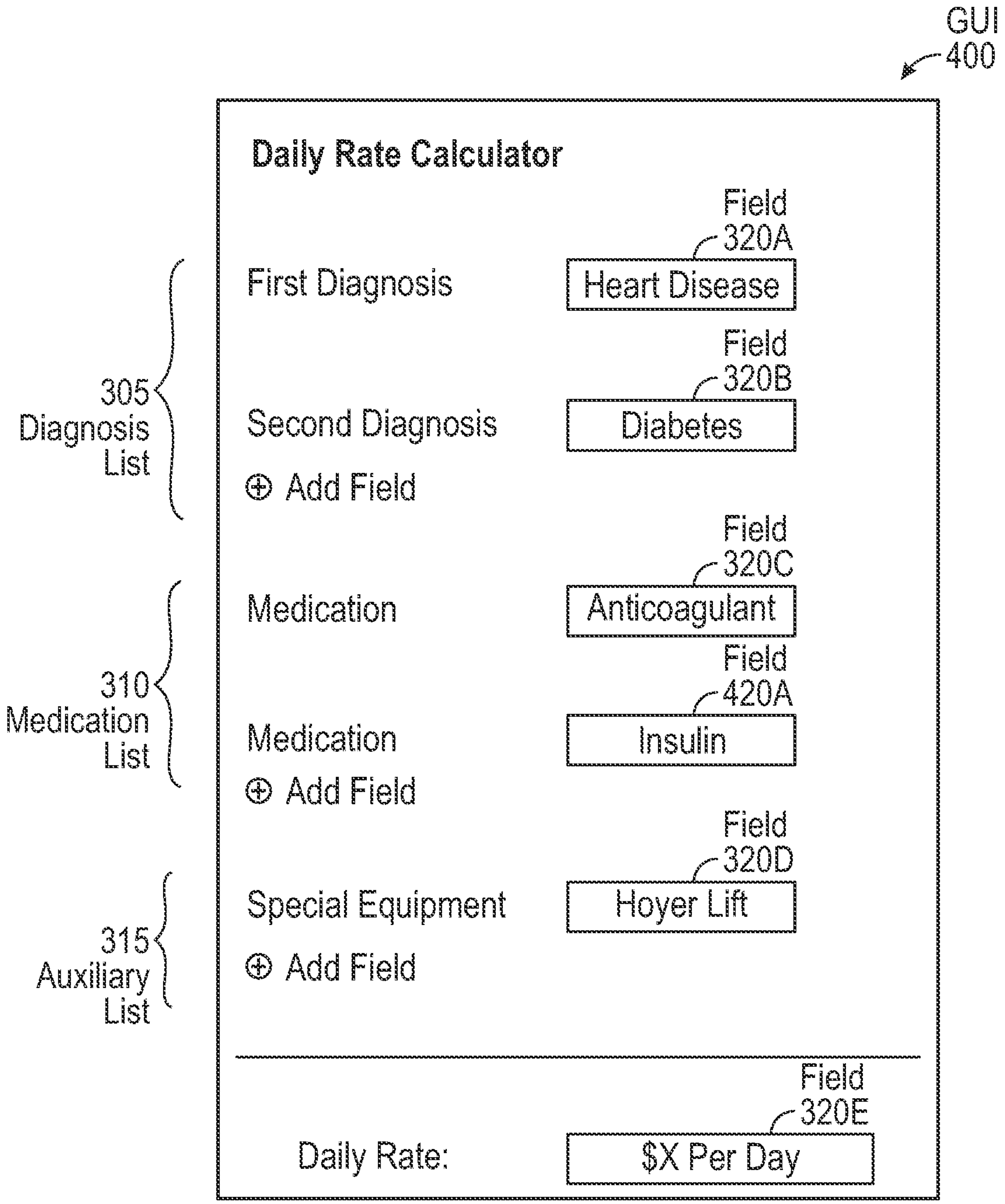

The calculator inputs 115 can include any of the information discussed above such as medical diagnoses, prescriptions, insurance, special medical equipment needed by the patient, and the like. In one embodiment, the daily calculator 120 may be defined or set by a payor. For example, the daily calculator 120 may be the PDPM calculator where its inputs are set by the CMS. If the parser 110 was able to identify all the inputs required by the PDPM calculator, then the calculator 120 is able to calculate the daily rate 125 without any human intervention from the evaluator 160 or the patient. Thus, the evaluation portal 105 can automatically identify the required inputs 115 for the daily calculator 120 using the parser 110 and generate the daily rate 125. However, if the parser 110 was unable to identify all the required inputs 115, the evaluator portal 105 can solicit help from a human—e.g., the evaluator 160—who can then review the medical records 150 to provide the missing calculator inputs 115. This is depicted in FIGS. 3 and 4.

In other embodiments, rather than the daily calculator 120 being defined by a particular payor (e.g., a government entity or insurance company), the daily calculator 120 can estimate the daily cost of being treated at the facility if the patient is paying out-of-pocket. For example, the healthcare facility may be a luxury addiction recovery center that is not covered by a patient's insurance. In that case, the daily rate calculator 120 can use the inputs 115 identified by the parser 110 (and any other required inputs) to calculate a daily rate 125 indicating the daily cost of the patient to stay at the facility.

The daily rate calculator 120 can include required inputs that are required before the daily rate 125 can be calculated as well as optional inputs that can be used to provide a more accurate daily rate 125, but are not required. For instance, in one example, the daily rate calculator 120 may require as inputs the patient's medical diagnosis and a corresponding prescription or medical treatment. However, the daily rate calculator 120 can also consider whether the patient requires any special medical equipment (e.g., a special lift). While the daily rate calculator 120 can calculate the daily rate 125 without knowing whether the patient needs any special equipment, the daily rate 125 may be more accurate if that information is provided.

As shown, the revenue calculator 130 uses the daily rate determined by the daily rate calculator 120 to generate a revenue stream 145, which is the predicted amount of total revenue generated as a result of the patient being admitted into the healthcare facility currently being evaluated. However, before the revenue stream 145 is determined, in one embodiment, the revenue calculator 130 uses a ML model 135 to predict or estimate the length of stay 140 of the patient at the facility.

In one embodiment, the ML model 135 predicts the length of stay using the diagnosis of the patient. Because the parser 110 often will have identified the patient's diagnosis when scanning the medical records 150 to identify the calculator inputs 115, the parser 110 can provide the patient's diagnosis (or diagnoses) to the ML model 135 automatically (without human intervention). Using the diagnosis as an input, the ML model 135 predicts the length of stay 140 such as, e.g., the number of days the patient will stay at the facility until being discharged. Stated differently, the length of stay 140 can be the length of time required before the patient will be healed and able to leave the facility (i.e., is discharges), either to go home or to be transferred to a different facility. In another example, the length of stay 140 can be the length of time before transitions to another level of care at the same facility. For example, if the patient had a hip fracture, the length of stay 140 can be the length of time the patient stays in the subacute unit until the fracture is resolved and the patient is transferred to a long term stay in another unit of the same facility.

The embodiments herein are not limited to any particular type of ML model. For example, the ML model 135 may be various types of neural networks. Further, the ML model 135 can be trained using historical records corresponding to patients that have previously been treated and discharged. This is discussed in more detail in FIGS. 7 and 8 below.

In addition to using the patient's diagnosis as an input, the ML model 135 can also consider other factors to predict the length of stay 140. For example, the ML model 135 may use the patient's age, weight, ethnicity, and the like since these factors may also affect how long it takes a patient to recover.

Once the length of stay 140 is estimated, the revenue calculator 130 determines the revenue stream 145 using the daily rate 125 and the length of stay 140. For example, the calculator 130 can multiply the daily rate 125 with the length of stay 140 to generate the revenue stream 145 (e.g., the total revenue predicted to result from the patient being admitted to the healthcare facility for treatment). As an example, if the daily rate 125 is $300 and the length of stay 140 is 10 days, then the revenue stream 145 may be $3000.

In some embodiments, the revenue calculator 130 provides a range of values for the revenue stream 145 rather than a single value. For example, the daily rate 125 or the length of stay 140 may be based on a range of values rather than a precise value. For example, the daily rate 125 may be a range between $300 and $400 per day. If the length of stay 140 is 10 days, then the revenue stream 145 may be estimated to be between $3,000 and $4,000. Alternatively, the ML model 135 may estimate a time range for the length of stay 140—e.g., the ML model 135 is 90% certain the length of stay 140 will be between 10-12 days. Assuming the daily rate 125 is $300, the revenue stream 145 may range from $3000 to $3600 in that example.

The GUI creator 155 outputs a GUI 165 that displays the daily rate 125, revenue stream 145, and the length of stay 140. However, in other embodiments, the GUI 165 may include a subset of these values—e.g., only the daily rate 125 and the revenue stream 145 but not the length of stay 140. Additionally, the GUI 165 can display other information such as the calculator inputs 115 parsed from the medical records 150 (e.g., the medical diagnoses, prescriptions, insurance, and special medical equipment needed by the patient), the medical records 150 themselves, and compatibility information or a compatibility score representing the compatibility between the patient and the healthcare facility (e.g., whether the facility can treat the patient's illness, or whether that facility has a special lift needed by the patient).

The GUI 165 can be viewed by the evaluator 160 or by the patient to then determine whether to recommend or choose the healthcare facility. For example, the evaluator 160 or the patient may use the evaluator portal 105 to evaluate and display GUIs 165 for a plurality of candidate healthcare facilities. The evaluator 160 or the patient can then select which one of the healthcare facilities is a best fit for the patient based on the financial information (e.g., the daily rate 125 and the revenue stream 145) and the compatibility information.

In one embodiment, the evaluation portal 105 includes an authentication system for ensuring only authorized individuals can access the GUI 165 which includes the patient's medical records 150. For example, the portal 105 may be accessible using a web browser, but the evaluator 160 must provide security credentials before the GUI 165 is displayed. In another embodiment, the evaluation portal 105 may be a secure application running locally (or natively) on the evaluator's computer device (e.g., a tablet, laptop, or desktop). The evaluation portal 105 may still require security credentials or biometric information (e.g., a face scan) before displaying the GUI 165 to ensure it is the evaluator 160 rather than a nefarious user who is attempting to access the patient's medical records 150.

Figure 2:
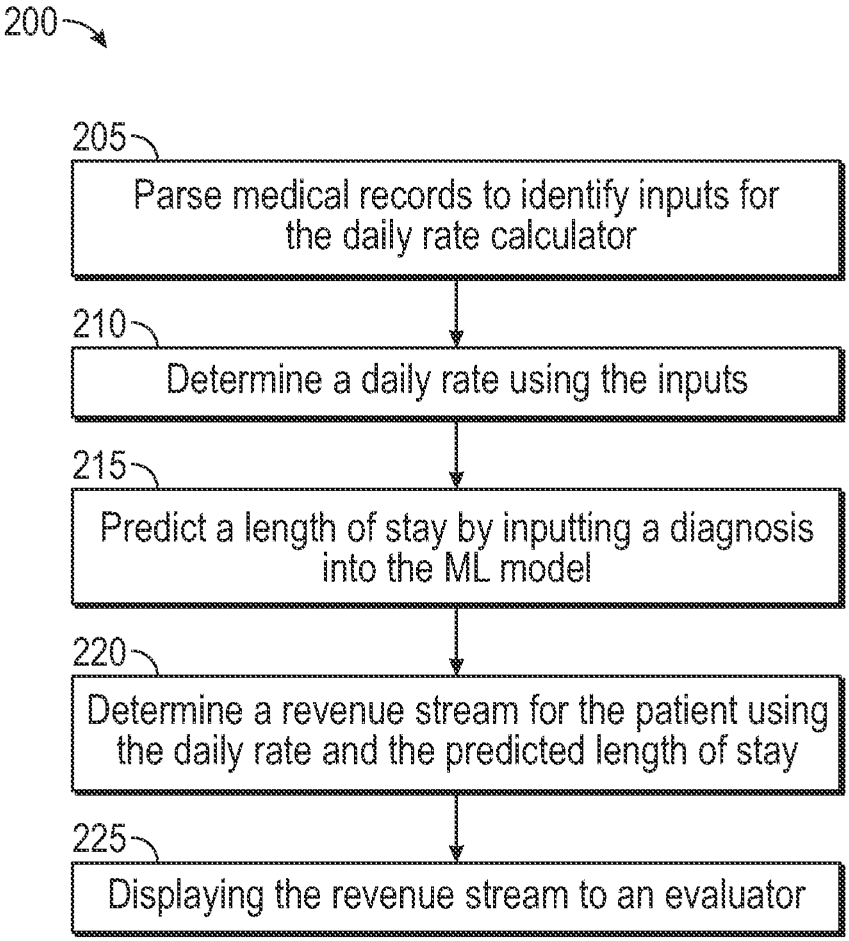
FIG. 2 is a flowchart for determining a daily rate and a revenue stream corresponding to a patient if admitted into a healthcare facility, according to one embodiment.

FIG. 2 is a flowchart of a method 200 for determining a daily rate and a revenue stream corresponding to a patient if admitted into a healthcare facility, according to one embodiment. At block 205, a parser (e.g., the parser 110 in FIG. 1) parses a patient's medical records to identify inputs for the daily rate calculator (e.g., the daily rate calculator 120 in FIG. 1). While the embodiments herein refer to a "patient", the method 200 can be used for by any person (regardless whether they are currently admitted into a healthcare facility). For example, the method 200 can be used by a person or a legal guardian to identify a healthcare facility for the person when that person is not currently in a healthcare facility. The person can use the method 200 to evaluate whether a particular facility, or which facility from a pool of candidate facilities, is a good fit for the person. However, for ease of explanation, the method 200 is described in the context of an evaluator (e.g., a healthcare professional or staff member) who is attempting to select a facility to transfer a current patient. The method 200 can also be used to determine that the patient should not be transferred a different facility. For example, the method 200 may indicate the patient's current facility is the best facility for the patient, and thus, she should not be transferred.

In one embodiment, when parsing the medical records, the parser performs a text search to identify relevant inputs for the daily rate calculator such as the patient's medical diagnosis, current prescriptions, special medical needs, payor information, and the like. In one embodiment, the parser includes a database of relevant medical information which is then compared to the text in the patient's medical records. If the medical records contain words that match an entry in the database, the parser then generates a calculator input (e.g., the calculator inputs 115 in FIG. 1) for the patient. For example, the database may list all the known medical diagnoses and their diagnosis codes. The parser can then parse the medical records to determine whether they contain text that matches one of the medical diagnoses or diagnosis codes stored in the database. If so, the parser generates a calculator input using that diagnosis. Similarly, the database may list all known drugs as well as medical treatments that do not use drugs (e.g., physical therapy treatments, surgeries, psychological treatments, etc.). The parser can scan the medical records to determine whether the patient is prescribed one of the drugs or is currently undergoing (or will undergo in the future) one of the medical treatments. If so, the parser can generate calculator inputs using those drugs and treatments.

In one embodiment, the medical record may list a medical diagnosis, drug, or treatment that does not exactly match an entry in the database. As such, the parser may use natural language processing (which can include the use of a ML model) to identify derivatives of the medical diagnoses, drugs, or treatments in the medical records. For example, the database may list "heart arrhythmia" but the medical records may instead recite "irregular heartbeat." Using natural language processing, the parser may determine that an irregular heartbeat matches heart arrhythmia, and in response, create a heart arrhythmia calculator input. Similarly, the text may use the plural form of the diagnoses or prescriptions. The parser can use natural language processing to still match these derivatives to the information in the database.

In yet another example, the medical records may recite the diagnoses in a different format than they are listed in the database. For example, the database recites "heart disease" but the medical records may recite the derivative "disease of the heart". Using natural language processing, the parser can identify and correlate the various different derivatives for the ailments, diagnoses, prescriptions, drugs, and medical treatments listed in the database with the text in the medical records.

In one embodiment, performing natural language processing can include the use of ML models (which may be different than the ML model 135 in the FIG. 1) to correlate the information in the medical records with the information in the database to generate the calculator inputs. For example, the parser can use a ML model that is trained to recognize the various derivatives of ailments, diagnoses, prescriptions, drugs, and medical treatments. In this manner, the medical records do not have to have medical information that precisely aligns with the information listed in the database in order to identify and generate the calculator inputs.

At block 210, the daily rate calculator determines a daily rate using the inputs identified at block 205. In one embodiment, the algorithm used by the daily rate calculator is provided by, or set by, the patient's payor (e.g., a government entity or a private insurer). The daily rate may indicate the amount the payor will reimburse (or pay) the healthcare facility per day for treating the patient. However, the embodiments herein can calculate a reimbursement or cost rate over different periods of times such as a weekly rate or an hourly rate.

In another embodiment, the daily rate calculator outputs the daily cost of treating the patient at the facility. This may be helpful when the payor does not set the daily rate or when the patient will pay out-of-pocket for the treatment. In this case, the algorithm used by daily the rate calculator may be provided by, or set by, the healthcare facility. In one embodiment, each healthcare facility (or each type of healthcare facility) may use a different daily rate calculator. For example, it may cost more to treat the same ailment at a hospital than at a skilled nursing center. Thus, the evaluator portal may use a different daily rate calculator depending on what type of healthcare facility is currently being evaluated.

If at block 205 the parser was able to identify all the inputs required by the daily rate calculator, then at block 210 the daily rate calculator is able to calculate the daily rate without any human intervention. Thus, the method 200 can automatically identify the required inputs at block 205 for the daily calculator using the parser and generate the daily rate at block 210. However, if the parser was unable to identify all the required inputs for the daily rate calculator, the method 200 can solicit help from a human—e.g., the evaluator—who can then review the medical records to provide the missing calculator inputs. Prompting the evaluator (or other person) to provide the missing information is described in the GUIs in FIGS. 3 and 4 below.

Further, the daily rate calculator can include required inputs that are needed before the daily rate can be calculated, as well as optional inputs that can be used to provide a more accurate daily rate, but are not required. For instance, in one example, the daily rate calculator may require as inputs the patient's medical diagnosis and a corresponding prescription or medical treatment. However, the daily rate calculator can also consider whether the patient requires any special medical equipment (e.g., a special lift). While the method 200 can calculate the daily rate without knowing whether the patient needs any special equipment, the daily rate may be more accurate if that information is provided.

At block 215, the ML model (e.g., the ML model 135 in FIG. 1) predicts a length of stay using the patient's diagnosis as an input. Because the method 200 may have identified the patient's diagnosis when parsing the medical records at block 205, the parser can provide the patient's diagnosis (or diagnoses) to the ML model. Otherwise, the diagnosis can be provided by the evaluator or the patient.

Using the diagnosis as an input, the ML model predicts the length of stay such as, e.g., the number of days or weeks the patient will stay at the facility until being discharged. Stated differently, the length of stay can be an estimate of the length of time required before the patient will be sufficiently healed and able to leave the facility, either to go home or to be transferred to a different facility. For example, the ML model may predict that a length of stay of a patient with Disease A is 8 days, but a patient with Disease B is 14 days. Further, in one embodiment, the ML model 135 can generate a predicted length of stay for a patient with multiple diagnoses. For example, the ML model may predict that a patient with both Diseases A and B will have a length of stay of 18 days.

In addition to using the diagnosis as an input, the ML model can also consider other factors to predict the length of stay. For example, the ML model may use the patient's age, weight, ethnicity, and the like since these factors may also affect how long it takes a patient to recover. Further, the ML model may also consider the type of healthcare facility being evaluated. For example, when being trained, the ML model may learn that patients may heal quicker for the same disease at different types of healthcare facilities. Thus, the ML model may predict that the length of stay of the patient at a hospital is different than the length of stay of the same patient with the same diagnosis at a skilled nursing center.

At block 220, the revenue calculator (e.g., the revenue calculator 130 of FIG. 1) determines a revenue stream for the patient using the daily rate and the predicted length of stay. For example, the calculator can multiply the daily rate with the length of stay to generate the revenue stream (e.g., the total revenue predicted to result from the patient being admitted to the healthcare facility for treatment). As an example, if the daily rate 125 is $300 and the length of stay 140 is 10 days, then the revenue stream 145 may be $3000.

In some embodiments, the revenue calculator provides a range of values for the revenue stream rather than a single value. For example, the daily rate or the length of stay may be based on a range of values rather than a precise value. For example, the daily rate may be a range between $300 and $400 per day. If the length of stay is 10 days, then the revenue stream 145 may be estimated to be between $3,000 and $4,000. Alternatively or additionally, the ML model 135 may estimate a time range for the length of stay which can also result in a range of values for the revenue stream.

At block 225, the evaluator portal displays the revenue stream to an evaluator, patient, legal guardian, etc. In one embodiment, a GUI creator (e.g., the GUI creator 155 in FIG. 1) generates a GUI with the revenue stream along with other information such as the daily rate, the length of stay, and the calculator inputs. Moreover, the GUI can also include compatibility information representing whether the facility has the equipment and expertise to treat the patient (e.g., whether the facility can treat the patient's illness, or whether that facility has a special lift needed by the patient).

In one embodiment, the evaluator portal transmits the GUI for display. For example, the GUI may be displayed in a web browser on a user device. Or the evaluator portal may be part of an application (app) executing on a user device. In any case, because the GUI can include private health information, the evaluator portal may require the evaluator to perform an authentication process before being shown the GUI.

FIGS. 3 and 4 are GUIs displaying a daily rate calculator, according to one embodiment. The GUI 300 in FIG. 3 illustrates displaying the calculator inputs used by the daily rate calculator to determine the daily rate. As shown, the GUI 300 includes a diagnosis list 305, a medication list 310, and an auxiliary list 315. The diagnosis list 305 includes a first diagnosis in a first field 320A and a second diagnosis in a second field 320B. In one embodiment, these diagnoses were identified by the parser at block 205 of the method 200. That is, when scanning the patient's medical record, the parser determined the patient had two current diagnoses, and in response, the GUI creator automatically populated the fields 320A and 320B to list these diseases. In this manner, the system can identify a patient with comorbidities where the patient simultaneously has two or more diseases or medical conditions.

The diagnosis list 305 also includes an "Add Field" which is a selectable link (i.e., a selectable element) that permits the user (e.g., the evaluator) to add a third diagnosis field to the list 305. When selected, the user may type in a third diagnosis into the new field or select a different diagnosis from a searchable list of candidate diagnoses. Further, if the parser misdiagnosed the patient (e.g., the patient previously had one of the diagnoses but has recovered), the GUI 300 can include a feature to edit or remove a diagnosis from the list 305.

The medication list 310 includes a first medication corresponding to a third field 320C. However, the text "NONE FOUND" indicates to the user that the parser was unable to identify any medications currently being taken by the patient when scanning the records at block 205 of the method 200. In this example, it is assumed that this missing information prevents the daily rate calculator from being able to calculate the daily rate. Thus, the field 320E corresponding to the daily rate has the text "MISSING INFORMATION". This informs the user that there are one or more calculator inputs that are required but are missing—i.e., the parser was unable to locate these inputs.

In one embodiment, the "NONE FOUND" in the field 320C indicates to the evaluator this field needs information before the daily rate can be calculated. IN another example, the text in the field 320C may state "MISSING—AT LEAST ONE MEDICATION OR TREATMENT MUST BE LISTED" to inform the evaluator what information she must provide in order to generate the daily rate. In one embodiment, the GUI 300 can use a visual indicator to indicate which required fields need to be filled in. The visual indicator can include coloring or highlighting the field 320C, adding a visual effect such as blinking, adding a pointer pointing to the field 320C, and the like. This can prompt the user to type in a medication into the field 320C or select a medication from a list of candidate medications.

In one embodiment, the daily rate calculator may require certain inputs based on other inputs already found by the parser. For example, because the parser identified the diagnoses of "HEART DISEASE" and "DIABETES", the daily rate calculator may know there are medications associated with these ailments, and thus, will not generate the daily rate until the medication field is populated. However, for other diagnoses, the daily rate calculator may not require the medication field to be filled in.

The medication list 310 also includes an "Add Field" which is a selectable link that permits the user (e.g., the evaluator) to add a second medication field to the list 310. When selected, the user may type in a second medication into the new field or select a different medication from a searchable list of candidate medications. Further, if the parser selected a medication for a different diagnosis than the ones listed in the diagnosis list 305, the GUI 300 can include a feature to edit or remove a medication from the list 310. For example, the evaluator may edit the field 320C to provide the missing medication.

The auxiliary list 315 includes special equipment corresponding to a fourth field 320D. The text in the field 320D indicates the user needs a Hoyer lift. The auxiliary list 315 also includes an "Add Field" which is a selectable link that permits the user (e.g., the evaluator) to add a second field to the list 315. When selected, the user may type in addition auxiliary information into the new field or select predefined medical equipment from a searchable list. Further, the GUI 300 can include a feature to edit or remove items from the list 315.

While the auxiliary list 315 includes special equipment used by the patient, the list 315 can include other auxiliary information such as frequent tests needed by the patient (e.g., CT scans or X-rays) or special lab work. This medical information can also affect the daily rate.

FIG. 4 illustrates a GUI 400 where a user (e.g., the evaluator) has provided the information that was missing in the GUI 300 in FIG. 3. In this example, the user has edited the field 320C to indicate the patient is taking an anticoagulant. Further, the user has leveraged the "Add Field" link in the medication list 310 to add a new field 420A and populated this new field 420A to indicate the patient is also taking insulin. The user could have typed in the medication into the field 420A, or selected insulin from a list of predefined medications.

Because the daily rate calculator now has the required inputs for calculating the daily rate, the field 320E now displays a rate—i.e., $X per day. This daily rate can indicate the amount a payor will reimburse the healthcare facility per day for treating the patient. In another embodiment, the daily rate can indicate an estimated cost to the healthcare facility per day. As discussed above, the algorithm for the daily rate calculator can be provided (or defined) by the payor. Alternatively, this algorithm can be a customized cost calculator for the healthcare facility.

Figure 5:
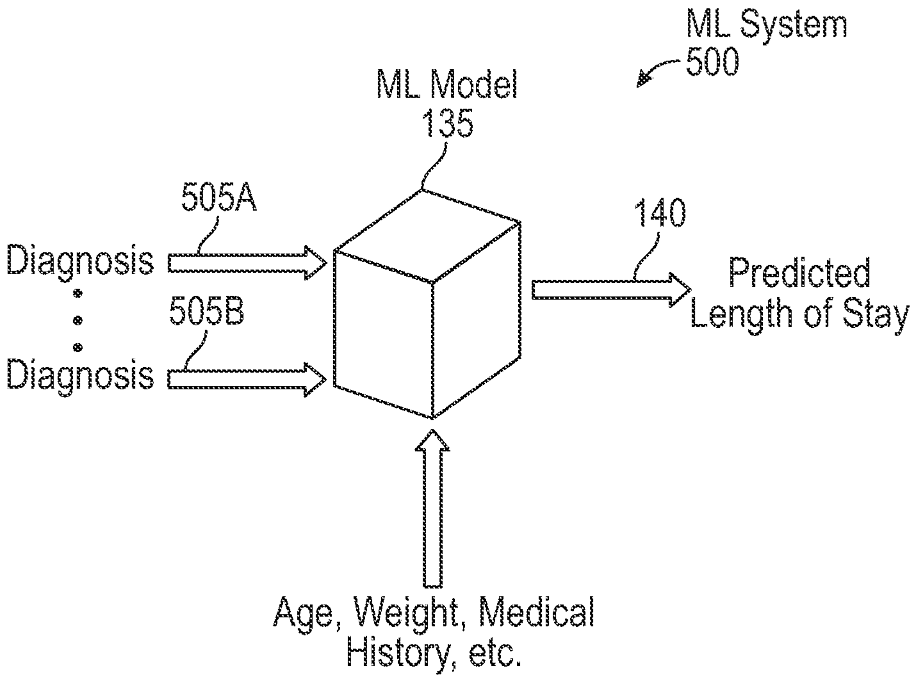
FIG. 5 is a ML system for predicting a revenue stream corresponding to a patient if admitted into a healthcare facility, according to one embodiment.

FIG. 5 is a ML system 500 for predicting a revenue stream corresponding to a patient if admitted into a healthcare facility, according to one embodiment. As shown, the ML model 135 predicts the length of stay using the diagnosis of the patient. Moreover, the ML model 135 can receive multiple diagnoses 505 for the patient. For example, the patient may have both heart disease and diabetes as indicated by the GUIs 300 and 400. As such, the ML model 135 can receive multiple diagnoses as inputs.

In one embodiment, the diagnoses 505 are provided by the parser. That is, because the parser often will have identified the patient's diagnosis 505 when scanning the medical records to identify the calculator inputs for the daily rate calculator, the parser can provide the patient's diagnosis 505 (or diagnoses) to the ML model 135. However, in other embodiments, the diagnoses 505 can be provided to the ML model 135 by the patient or the evaluator.

Using the diagnosis 505 as an input, the ML model 135 predicts the length of stay 140 such as, e.g., the number of days the patient will stay at the facility until being discharged. Stated differently, the length of stay 140 can be the length of time required before the patient will be healed and is transferred to a different unit in the facility or is able to leave the facility, either to go home or to be transferred to a different facility. The length of stay 140 can change depending on the type of diagnosis 505 as well as the combination of diagnoses 505. For example, the ML model 135 may determine that the length of stay 140 for Diagnosis A is 10 days, but the length of stay 140 for Diagnosis B is 14 days. If the patient has have both Diagnoses A and B, the length of stay 140 may be predicted as 18 days. Thus, the ML model 135 can predict the length of stay in response to one diagnosis, or a combination of several diagnoses.

As described later, the ML model 135 can be trained using historical medical records for patients. These records can indicate the diagnoses of these patients as well as their length of stay. From this, the ML model 135 can learn correlations between a particular diagnosis (or combination of diagnoses) and the length of stay.

In addition to using the diagnosis as an input, the ML system 500 indicates the ML model 135 can also consider other factors to predict the length of stay 140. For example, the ML model 135 may use the patient's age, weight, medical history, ethnicity, and the like since these factors may also affect how long it takes a patient to recover. For example, the ML model 135 may predict a longer length of stay 140 for an older patient who has the same diagnosis as a younger patient. Or the patient's weight or a history of previous diagnoses can result in the ML model 135 predicting a different length of stay 140 than if these factors were not input into the ML model 135.

The embodiments herein are not limited to any particular type of ML model. For example, the ML model 135 may be various types of neural networks.

Figure 6:
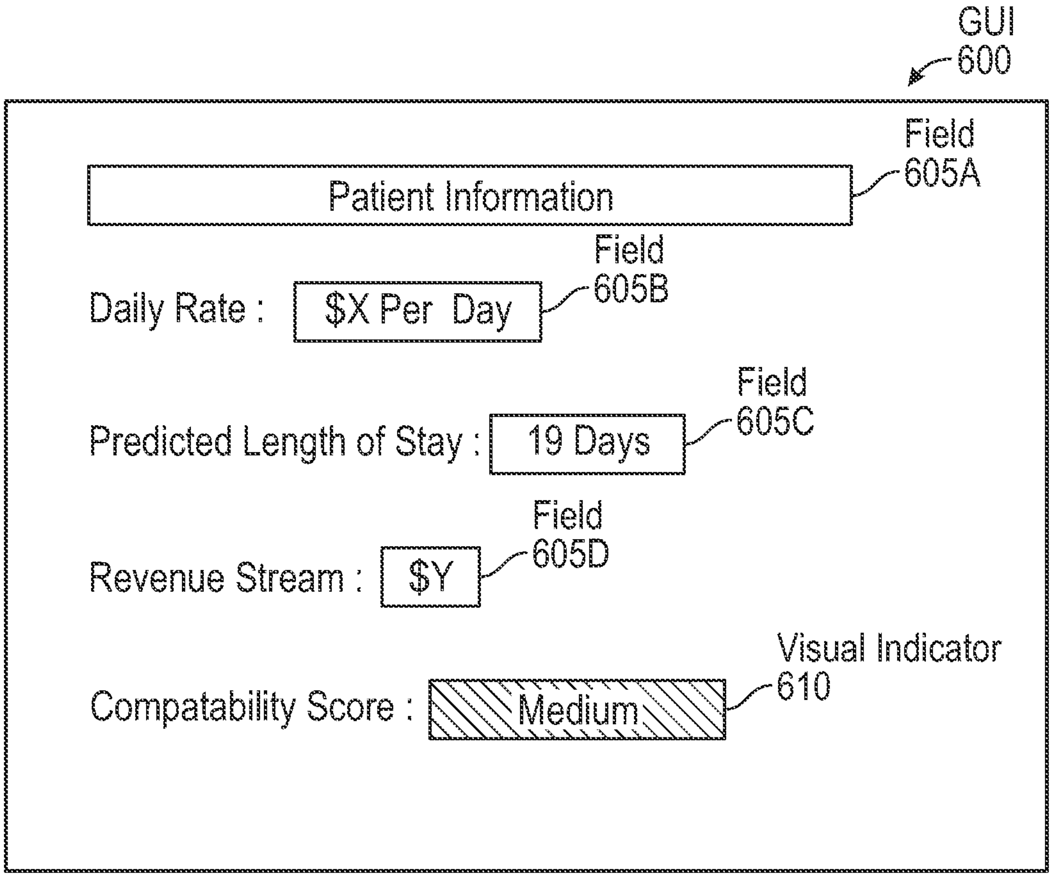
FIG. 6 is a graphical user interface displaying a predicted revenue stream for a patient at a healthcare facility, according to one embodiment.

FIG. 6 is a GUI 600 displaying a predicted revenue stream for a patient at a healthcare facility, according to one embodiment. In one embodiment, the GUI creator may generate the GUI 600 as part of block 225 in the method 200. For example, the GUI 600 may be a result of performing the method 200 to determine a revenue stream in response to calculating a daily rate and predicting a length of stay.

The top of the GUI 600 includes a field 605A which can display patient information. The patient information can include the name of the patient (i.e., the referral), date of birth, contact information, primary physician, emergency contact, and history of previous admissions. In one example, the field 605A may include a timeline illustrating healthcare facilities the patient has been admitted to previously, as well as the patient's current facility.

The patient information in the field 605A can also indicate medical information gleaned from the patient's medical records by the parser. For example, the field 605A may list the patient's current diagnosis, current medications, special medical equipment needed by the patient, frequency medical tests required by the patient, dietary restrictions, etc. This can inform the evaluator of the information identified by the parser, which may have been used to determine the daily rate.

In one embodiment, the evaluator portal highlights or emphasizes important medical information identified by the parser. For example, the diagnosis and the medication may be emphasized by being tagged separately in the field 605A from other medical information (e.g., the patient's dietary restrictions). The tagged information can be highlighted using bright colors, bolded text, italics, animations, and the like. In this manner, the important patient information can be emphasized at the top of the GUI 600.

The GUI 600 also includes the field 605B which displays the daily rate determined using the calculator inputs identified by the parser as well any inputs provided by the evaluator. For example, if the parser was able to determine all the required inputs for generating the daily rate, the evaluator portal may provide the GUI 600 automatically. However, if the parser was unable to identify all the required inputs for the daily rate calculator, then the evaluator portal may first output the GUI 300 to prompt the evaluator to provide the missing input. However, in other embodiments, the evaluator portal may output the GUI 300 regardless whether the parser could identify the required calculator inputs. Doing so provides the evaluator with the opportunity to double-check the inputs identified by the parser as well as provide the evaluator with a chance to manually add further inputs for the daily rate calculator.

The GUI 600 also includes the field 605C which indicates the length of stay predicted by the ML model. While the GUI 600 provides an exact predicted length of stay—i.e., 19 days—in another embodiment, the field 605C may include a time range such as 18-22 days. In another embodiment, the GUI 600 may also output a confidence score in the length of stay. For example, the ML model may output a confidence score (e.g., a percentage) indicating how confident it is in the length of stay. The GUI 600 can then output that confidence score to the evaluator.

The field 605D provides the revenue stream for the patient if admitted into the healthcare facility. In one embodiment, the revenue calculator determines the revenue stream by multiplying the daily rate in the field 605B with the length of stay in field 605C. In other embodiments, the revenue calculator considers other factors in addition to the daily rate and the revenue stream. For example, the revenue calculator may consider out-of-pocket payments from the patient.

Further, the GUI 600 includes a visual indicator 610 for representing a compatibility score between the patient and the healthcare facility. For example, the medical information learned by the parser indicates the patient needs a lift, and the facility has the lift, the visual indicator 610 may be assigned the color green. However, if the facility does not have the lift, the visual indicator 610 may be assigned the color red. For situations where the compatibility scores are somewhere between completely compatible and compatibility incompatible, the visual indicator 610 may be assigned the color yellow or orange. For example, if patient's medical information indicates the patient needs frequent CT scans but the facility offers CT scans on a limited time schedule or has a limited number of CT machines, the visual indicator 610 may be assigned the color yellow. Or if the patient has an insurance provider that is accepted, but not preferred by the facility, the visual indicator 610 may be assigned the color yellow.

In one embodiment, the compatibility score may be range of values on a sliding scare (e.g., from 1-10 or from 1-100). Attributes of the healthcare facility may associate different diagnoses, prescriptions, or medical treatments with different values of the sliding scale (e.g., the compatibility score). For instance, all diseases and ailments associated with the heart may be assigned a value of 10 indicating the facility specializes in those diseases. Thus, if the patient has heart disease, the compatibility score is assigned a value of 10 indicating very high compatibility. All other diseases and ailments associated with the cardiovascular system (but not specifically with the heart) may be assigned a value of 9 in the scale. All diseases and ailments associated with the respiratory system may be assigned a value of 8 in the scale, while all diseases and ailments associated with the musculoskeletal system and the nervous system are assigned a value of 7 in the scale, and so forth. In this manner, the diagnosis of the patient can be matched with a value in a sliding scale to result in the compatibility score, based on the attributes or capabilities of the particular healthcare facility being evaluated. This ranking can also be applied to other types of medical information such as patient's prescriptions and medical treatments to derive the compatibility score and assign the visual indicator 610.

Assigning colors to the visual indicator 610 is just one example of applying visual indicators. In other embodiments, the visual indicator 610 may be assigned different luminance values or different sizes in response to the compatibility score. In another embodiment, different highlighting or visual effects (e.g., blinking) can be applied to the visual indicator 610 to represent the patient's compatibility with a particular facility.

In other embodiments, the evaluator portal may display different information to the evaluator than what is shown in GUI 600. For example, it may be sufficient for the evaluator to make a decision by displaying only the daily rate and the revenue stream—i.e., the length of stay and the compatibility score can be omitted. In other embodiments, the evaluator portal may display a GUI at the end of the method 200 that has more information than the GUI 600. For example, the evaluator portal may provide the same information shown in the GUI 600 but for multiple healthcare facilities, rather than just one healthcare facility. Or the GUI includes tags that were identified by the parser when scanning the patient's medical records.

Figure 7:
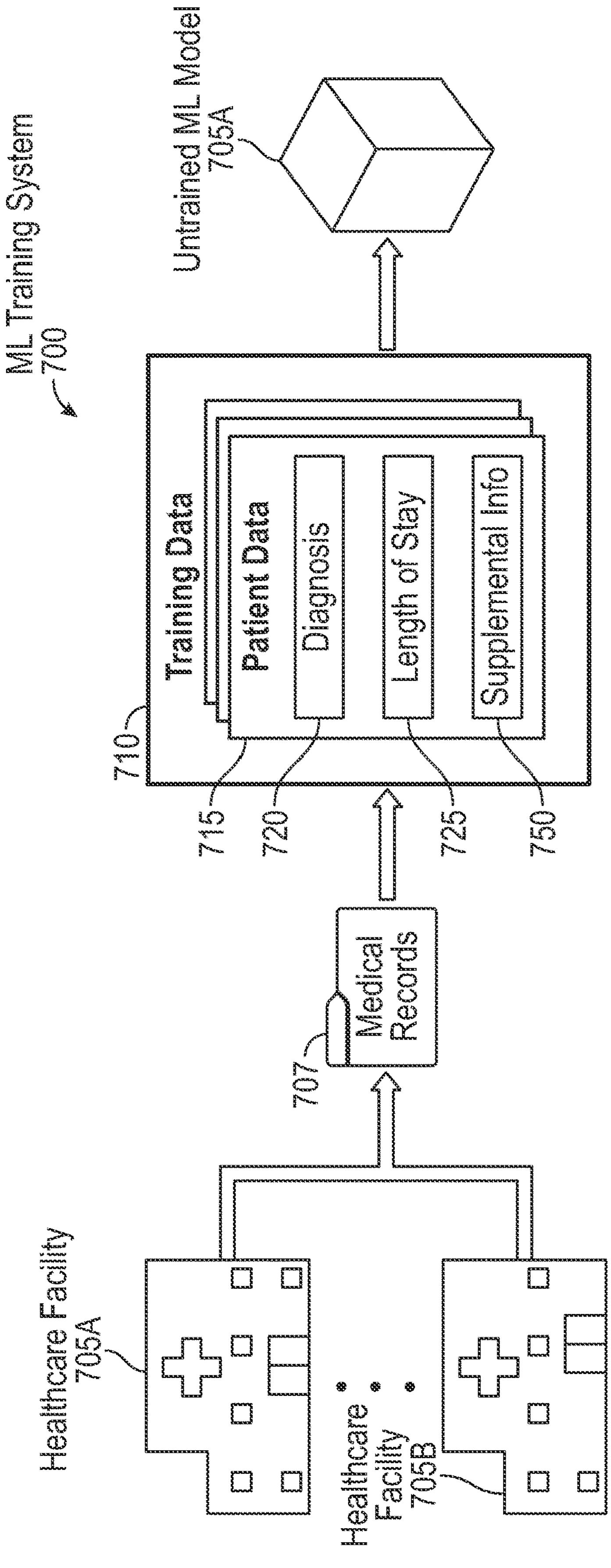
FIG. 7 illustrates a ML training system, according to one embodiment.

FIG. 7 illustrates a ML training system 700, according to one embodiment. The left of the ML training system 700 illustrates collecting medical records 707 from patients admitted into multiple healthcare facilities 705. That is, unlike the medical records 150 in FIG. 1, the medical records 707 can be associated with multiple patients previously admitted into multiple facilities 705. In one embodiment, the medical records 707 are for patients that have been discharged from the healthcare facilities 705.

Because the medical records 707 are used to trained an untrained ML model 735, the ML training system 700 may redact personal information from the medical records 707. For example, because the ML model 735 is being trained to learn the correlation between diagnosis (and potentially other information) and the length of stay, the personal information of the patients such as their names, phone numbers, addresses, etc. may be unnecessary. Thus, this information can be redacted or removed from the medical records 707 to improve security and provide anonymity.

While the ML training system 700 illustrates collecting medical records 707 from multiple facilities, the system 700 could train the ML model 735 using medical records 707 from just one facility. However, this may require collecting medical records over a longer period of time to have sufficient training data 710. Moreover, it may lead to a better trained model if the medical records 707 are collected from facilities that are in different geographic areas. Alternatively, it may be better if the ML model 735 is trained using medical records 707 from the same geographic region as the patient being evaluated in method 200. For example, the evaluator portal may have several ML models that are trained using medical records 707 collected from different geographic regions in a country. Depending on the location of the current patient being evaluator at method 200, the evaluator portal may select the ML model trained using medical records gathered from the same geographic region in order to predict the length of stay.

The ML training system 700 generates training data 710 using the medical records 707. In this example, the training data 710 includes patient data 715 for each patient identified in the medical records 707. The patient data 715 indicates the diagnosis 720 (or diagnoses) of the patient that was being treated at the healthcare facility 705 and the patient's length of stay 725 at the facility 705 before being discharged, transferred to a different unit in the same facility, or transferred to a different facility. Thus, unlike in method 200 where the ML model predicts the length of stay, here the length of stay 725 is a known factor so that, when the patient data 715 is input into the untrained ML model 735, it can learn the correlation between a particular diagnosis (or a combination of diagnoses) and the length of stay 725 of the patient.

Optionally, the patient data 715 can include supplemental information 730, such as the patient's age, weight, medical history, ethnicity, and the like since these factors may also affect how long it takes a patient to recover. In one embodiment, the supplemental information can also include the type of the healthcare facilities 705 being evaluated. For example, when being trained, the ML model 735 may learn that patients may heal quicker for the same disease at different types of healthcare facilities. Thus, the ML model may predict that the length of stay of the patient at a hospital is different than the length of stay of the same patient with the same diagnosis at a skilled nursing center.

However, identifying the supplemental information 730 from the medical records 707 is not a requirement. That is, the ML model 735 can be trained solely using the diagnosis 720 and the length of stay 725.

In one embodiment, the ML training system 700 may generate training data only for the patients that were discharged rather than those that passed away while in the healthcare facility 705. That is, the training data 710 may include only the patients who recovered from the diagnosis 720.

The right side of FIG. 7 illustrates training the ML model 735 using the training data. As a result of training the model 735, the ML training system 700 can generate a trained ML model (e.g., the ML model 135 in FIG. 1) that can be used during an inference stage to predict a length of stay of a patient based on any number of factors such as the patient's diagnosis, age, weight, and the like.

Figure 8:
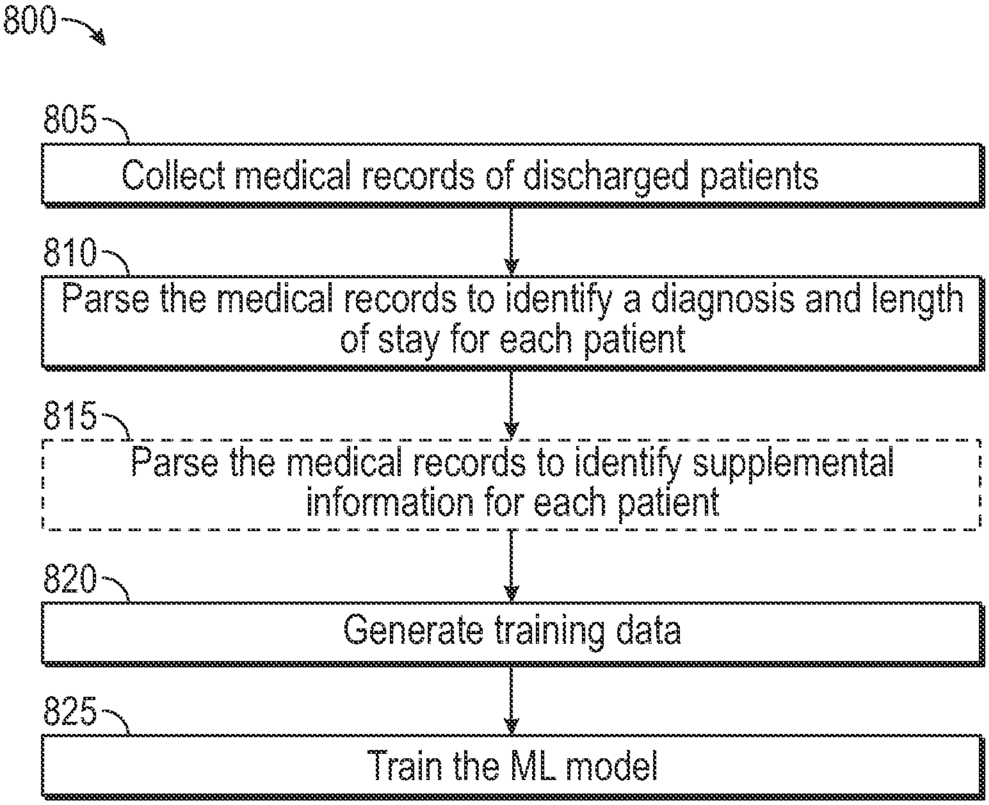
FIG. 8 is a flowchart for training a ML model, according to one embodiment.

FIG. 8 is a flowchart of a method 800 for training a ML model, according to one embodiment. At block 805, a ML training system (e.g., the ML training system 700 in FIG. 7) collects medical records of discharged patients. In one embodiment, the system gathers records from a plurality of healthcare facilities. These healthcare facilities can be part of the same healthcare provider. Alternatively, the ML training system can collect medical records from facilities operated by multiple, different healthcare providers. Further, instead of collecting medical records from a plurality of healthcare facilities, the medical records could be collected from a single healthcare facility.

If the medical records are collected from multiple healthcare facilities, in one embodiment, the ML training system may group the medical records into different geographic regions. For example, the medical records collected from healthcare facilities in a first geographic region (e.g., the Southeast of the United States) are assigned to a first group, the medical records collected from healthcare facilities in a second geographic region (e.g., the Southwest of the United States) are assigned to a second group, and so forth. Because the characteristics of the people and environments in a region may differ (e.g., different diets, lifestyles, climate, etc.), the ML training system may separate the medical records based on geographic regions and train different ML models for each region. However, in another embodiment, all the medical records may be assigned to the same group, regardless of the geographic location of the healthcare facilities.

At block 810, the ML training system parses the medical records to identify a diagnosis and length of stay for each patient. The system can use a keyword search and natural language processing to identify the diagnosis and the length of stay. For example, the same techniques used by the parser 110 in FIG. 1 to identify the calculator inputs 115 can also be used here to identify the diagnosis and the length of stay.

In one embodiment, pre-processing the data in the medical records may improve the ML training process by making the data more compatible with natural language processing, and ultimately for consumption by the ML model during training. Pre-processing can include tokenization where strings of text are splitting into smaller strings or "tokens." For example, paragraphs can be tokenized into sentences and sentences can be tokenized into words. Pre-processing can also include normalization to, e.g., converting all characters to lowercase, converting accented characters to ASCII characters, expand contractions, convert words to numeric form, etc. Pre-processing can also include noise removal such as removing extra white spaces, HTML tags, etc. Pre-processing can also include lemmatization or stemming where a word is converted to its base form such as "holding" to "hold." Pre-processing can further include text identification and text elimination of redundant words or the reduction of a sentence or phrase to the portions that are most suitable for machine learning training or application, e.g. elimination of verbs, conjunction or other extraneous words and/or reducing a phrase or sentence to its most relevant bigram or root during any relevant steps of machine learning training and/or application. Pre-processing can further include any other suitable technique for making text ingestion (either in a training phase of an ML or with respect to data ingested after training to render a prediction).

In one embodiment, the pre-processed text is converted into an object that can be represent numerically. For example, one-hot encodings and word embedding vectors can be used. The resulting object can then be processed by the natural language processing algorithm to improve its ability to identify the diagnosis and the length of stay. Improving the results of the natural language processing algorithm can have a positive impact on the accuracy of training the ML model.

In some embodiments, the medical records may indicate the patient has several diagnoses. The ML training system can determine which diagnosis contributed to the length of stay. For example, a patient may be diagnosed with both a bacterial infection and diabetes. However, the ML training system may determine that the reason the patient was admitted in the healthcare facility was because of the infection. For example, the ML training system may look for words or phrases in the medical record indicating that the infection was treated. In another example, the ML training system may determine that when the patient was admitted to the hospital she was diagnosed with the infection and diabetes, but when she was discharged she no longer had the infection but still has diabetes. Thus, the ML training system may determine that the length of stay in the facility was due to the infection but not the diabetes.

In contrast, if the system identifies multiple diagnoses in the medical record, if the medical record indicates all the diagnoses were treated, or the patient recovered from the diagnoses, then the ML training system determines that the length of stay was due to all of the diagnoses. For example, if when being admitted to the facility the patient's medical record indicated she had two diseases, but when discharged, she did not have either disease, then the system can correlate the length of stay to both diseases, rather than just one disease. In this manner, if a patient has comorbidities, the ML training system can determine whether one, some, or all of the comorbidities contributed to length of stay of the patient in the healthcare facility.

In one embodiment, ML training system redacts personal information from the medical records. For example, because the ML model is being trained to learn the correlation between diagnosis (and potentially other information) and the length of stay, the personal information of the patient such as her name, phone number, address, etc. may be unnecessary. Thus, this information can be redacted or removed from the medical records by the ML training system to improve security and provide anonymity.

At block 815 (which is an optional step), the ML training system parses the medical records to identify supplemental information for each patient. This supplemental information can be a patient's age, weight, medical history, ethnicity, or the type of healthcare facility from which the medical records were obtained. Because this information may also affect the length of stay of a patient, the method 800 can optionally use this information to train the ML model. However, this is not required and the ML model can instead be trained solely using the diagnosis (or diagnoses) and the length of stay.

At block 820, the ML training system generates training data using the information identified at block 810 and optionally at block 815. For example, the training data may include separate files or entries for each patient in the collected medical records. The files or entries can each list the patient's diagnosis (or diagnoses) and the length of stay in the facility. Notably, if the ML training system identified multiple diagnoses for the patient but also determined one of those diagnoses did not contribute to the patient's length of stay, then the system may omit that diagnosis from the training data. Using the example above, if the patient was diagnosed was both a bacterial infection and diabetes but it was the infection that caused the patient to be admitted into the hospital (e.g., the diabetes is a chronic condition that the patient already had under control), then the length of stay in the facility may be correlated only to the infection. Thus, in the training data, the patient's file may list only the infection and omit diabetes. That way, the ML model is not trained with data indicating the patient's stay at the facility was to treat diabetes.

The files or entries for the patients can also include the supplemental information such as the patient's age, weight, medical history, ethnicity, and the like. In general, the training data formats the relevant information parsed from the medical records into a format that is digestible to the untrained ML model.

At block 825, the ML training system trains the ML model. That is, the diagnosis and supplemental information can be used as inputs to the ML model to perform a supervised learning process. That is, the training data is labeled training data that contains a set of training examples (i.e., the patient files or entries) where the length of stay is the desired output value (e.g., the supervisory signal). In this manner, the medical records for multiple patients can be used to train the ML model.

In one embodiment, the ML training system may train multiple ML models. For example, if the method 800 assigned the medical records to separate groups based on geographic regions, the training data derived from the separate groups can be used to train separate ML models. That is, the method 800 can be used to train a ML model to predict length of stays for patients at different geographic regions. These predictions may be more accurate than using a single ML model that does not consider geographic regions.

Once trained, the ML model can then be used in the embodiments discussed above to predict a length of stay. That is, the trained ML model can be used at block 215 of the method 200 to predict a length of stay using a diagnosis (as well as other supplemental information) as an input.

Example Computing Hardware

Figure 9:
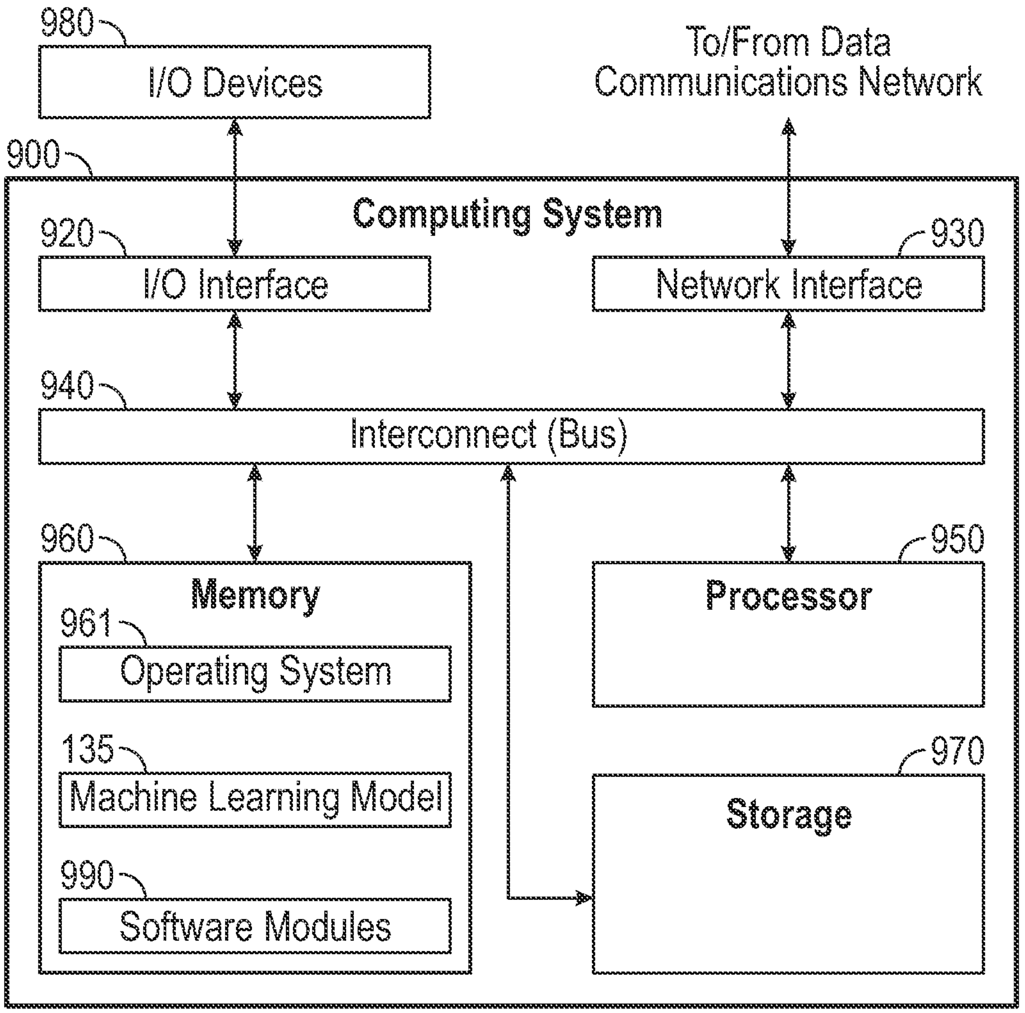
FIG. 9 illustrates a computing system, according to one embodiment.

FIG. 9 illustrates a computing system 900, which may be used to implement the evaluation portal 105 in FIG. 1 or the ML training system 700 in FIG. 7 (e.g., a computer, a laptop, a tablet, a smartphone, web server, data center, cloud computing environment, etc.), or any other computing device described in the present disclosure. As shown, the computing system 900 includes, without limitation, a computer processor 950 (e.g., a central processing unit), a network interface 930, and memory 960. The computing system 900 may also include an input/output (I/O) device interface 920 connecting I/O devices 980 (e.g., keyboard, display and mouse devices) to the computing system 900.

The processor 950 retrieves and executes programming instructions stored in the memory 960 (e.g., a non-transitory computer readable medium). Similarly, the processor 950 stores and retrieves application data residing in the memory 960. An interconnect 940 facilitates transmission, such as of programming instructions and application data, between the processor 950, I/O device interface 920, storage 970, network interface 930, and memory 960. The processor 950 is included to be representative of a single processor, multiple processors, a single processor having multiple processing cores, and the like. And the memory 960 and the storage 970 are generally included to be representative of volatile and non-volatile memory elements. For example, the memory 960 and the storage 970 can include random access memory and a disk drive storage device. Although shown as a single unit, the memory 960 or the storage 970 may be a combination of fixed and/or removable storage devices, such as magnetic disk drives, flash drives, removable memory cards or optical storage, network attached storage (NAS), or a storage area-network (SAN). The storage 970 may include both local storage devices and remote storage devices accessible via the network interface 1030. One or more ML models 135 are maintained in the memory 960 to predict the length of stay of a patient at a healthcare facility. Additionally, one or more software modules 990 may be maintained in the memory to perform the functions of the parser 110, daily rate calculator 120, revenue calculator 130, and the GUI creator 155 discussed above.

Further, the computing system 900 is included to be representative of a physical computing system as well as virtual machine instances hosted on a set of underlying physical computing systems. Further still, although shown as a single computing device, one of ordinary skill in the art will recognize that the components of the computing system 900 shown in FIG. 9 may be distributed across multiple computing systems connected by a data communications network.

As shown, the memory 960 includes an operating system 961. The operating system 961 may facilitate receiving input from and providing output to various components. For example, the network interface 930 can be used to output the GUIs 300, 350, and 400 discussed above. In another example, the network interface 930 can be used to receive medical records from patients who have been discharged in order to train the ML model 135 as discussed in method 800.

Additional Considerations

The preceding description is provided to enable any person skilled in the art to practice the various embodiments described herein. The examples discussed herein are not limiting of the scope, applicability, or embodiments set forth in the claims. Various modifications to these embodiments will be readily apparent to those skilled in the art, and the generic principles defined herein may be applied to other embodiments. For example, changes may be made in the function and arrangement of elements discussed without departing from the scope of the disclosure. Various examples may omit, substitute, or add various procedures or components as appropriate. For instance, the methods described may be performed in an order different from that described, and various steps may be added, omitted, or combined. Also, features described with respect to some examples may be combined in some other examples. For example, an apparatus may be implemented or a method may be practiced using any number of the aspects set forth herein. In addition, the scope of the disclosure is intended to cover such an apparatus or method that is practiced using other structure, functionality, or structure and functionality in addition to, or other than, the various aspects of the disclosure set forth herein. It should be understood that any aspect of the disclosure disclosed herein may be embodied by one or more elements of a claim.

As used herein, the word "exemplary" means "serving as an example, instance, or illustration." Any aspect described herein as "exemplary" is not necessarily to be construed as preferred or advantageous over other aspects.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

The methods disclosed herein comprise one or more steps or actions for achieving the methods. The method steps and/or actions may be interchanged with one another without departing from the scope of the claims. In other words, unless a specific order of steps or actions is specified, the order and/or use of specific steps and/or actions may be modified without departing from the scope of the claims. Further, the various operations of methods described above may be performed by any suitable means capable of performing the corresponding functions. The means may include various hardware and/or software component(s) and/or module(s), including, but not limited to a circuit, an application specific integrated circuit (ASIC), or processor. Generally, where there are operations illustrated in figures, those operations may have corresponding counterpart means-plus-function components with similar numbering.

The following claims are not intended to be limited to the embodiments shown herein, but are to be accorded the full scope consistent with the language of the claims. Within a claim, reference to an element in the singular is not intended to mean "one and only one" unless specifically so stated, but rather "one or more." Unless specifically stated otherwise, the term "some" refers to one or more. No claim element is to be construed under the provisions of 35 U.S.C. § 112(f) unless the element is expressly recited using the phrase "means for" or, in the case of a method claim, the element is recited using the phrase "step for." All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims.

Clause 1: A method comprising parsing, using one or more computer processors, a medical record for a patient to identify an input to a rate calculator, determining, using the rate calculator, a reimbursement or cost rate of the patient at a healthcare facility based on the identified input, predicting, using a machine learning (ML) model, a length of stay of the patient based on a diagnosis of the patient, and determining, before the patient is admitted into the healthcare facility, a revenue stream corresponding to the patient based on the reimbursement or cost rate and the predicted length of stay.

Clause 2: In addition to the clause 1, further comprising determining, after parsing the medical record, that a required input to the rate calculator is missing, transmitting for display a graphical user interface (GUI) indicating the required input is missing, the GUI display a first field by which a user can provide the required input, and receiving the required input via the GUI, wherein the reimbursement or cost rate is determined after receiving the required input.

Clause 3: In addition to the clause 2, wherein the GUI comprises (i) a second field that is automatically populated to include the identified input and (ii) a selectable element permitting the user to provide an additional input for the rate calculator using a third field.

Clause 4: In addition to the clause 3, further comprising, after determining the reimbursement or cost rate: transmitting for display a second GUI containing the first field, the second field, and the reimbursement or cost rate, wherein the reimbursement or cost rate is calculated using information in the first and second fields, wherein the information comprises at least one of a diagnosis or medication corresponding to the patient.

Clause 5: In addition to the clauses 1, 2, 3, or 4, further comprising, before predicting the length of stay: parsing the medical record for the patient to identify the diagnosis to use as an input to the ML model.

Clause 6: In addition to the clause 5, further comprising, before predicting the length of stay: parsing the medical record for the patient to identify supplemental information to use as an input to the ML model to predict the length of stay, the supplemental information comprising at least one an age or weight of the patient.

Clause 7: In addition to the clauses 1, 2, 3, 4, 5, or 6 further comprising, before predicting the length of stay: receiving medical records for a plurality of patients previously discharged from at least one healthcare facility; parsing the medical records to identify a diagnosis and a length of stay of each of the plurality of patients at the at least one healthcare facility; generate training data based on the diagnosis and the length of stay of each of the plurality of patients at the at least one healthcare facility; and training the ML model using the training data.

Clause 8: In addition to the clause 7, further comprising, before predicting the length of stay: parsing the medical records to identify supplemental information of each of the plurality of patients at the at least one healthcare facility, the supplemental information comprising at least one of an age or weight of each of the plurality of patients; and training the ML model using the age or weight of each of the plurality of patients.

Clause 9: In addition to the clause 7, wherein parsing the medical records to identify the diagnosis and the length of stay of each of the plurality of patients at the at least one healthcare facility comprises: pre-processing the medical records by tokenizing the text in the medical records and normalizing the tokenized text.

Clause 10: In addition to the clause 9, wherein pre-processing the medical records further comprises: converting the tokenized text into an object that is represented numerically using at least one of one-hot encodings or word embedding vectors; and processing the object using a natural language processing algorithm.

Clause 11: A non-transitory computer readable medium comprising instructions to be executed in a processor, the instructions when executed in the processor perform an operation, the operation comprising: parsing a medical record for a patient to identify an input to a rate calculator; determining, using the rate calculator, a reimbursement or cost rate of the patient at a healthcare facility based on the identified input; predicting, using a machine learning (ML) model, a length of stay of the patient based on a diagnosis of the patient; and determining, before the patient is admitted into the healthcare facility, a revenue stream corresponding to the patient based on the reimbursement or cost rate and the predicted length of stay.

Clause 12: In addition to the clause 11, wherein the operation further comprises: determining, after parsing the medical record, that a required input to the rate calculator is missing; transmitting for display a graphical user interface (GUI) indicating the required input is missing, the GUI display a first field by which a user can provide the required input; and receiving the required input via the GUI, wherein the reimbursement or cost rate is determined after receiving the required input.

Clause 13: In addition to the clause 15, wherein the GUI comprises (i) a second field that is automatically populated to include the identified input and (ii) a selectable element permitting the user to provide an additional input for the rate calculator using a third field.

Clause 14: In addition to the clause 13, wherein the operation further comprises, after determining the reimbursement or cost rate: transmitting for display a second GUI containing the first field, the second field, and the reimbursement or cost rate, wherein the reimbursement or cost rate is calculated using information in the first and second fields, wherein the information comprises at least one of a diagnosis or medication corresponding to the patient.

Clause 15: In addition to the clauses 11, 12, 13, or 14, wherein the operation further comprises, before predicting the length of stay: parsing the medical record for the patient to identify the diagnosis to use as an input to the ML model.

Clause 16: In addition to the clause 15, wherein the operation further comprises, before predicting the length of stay: parsing the medical record for the patient to identify supplemental information to use as an input to the ML model to predict the length of stay, the supplemental information comprising at least one an age or weight of the patient.

Clause 16: In addition to the clauses 11, 12, 13, 14, or 15, wherein the operation further comprises, before predicting the length of stay: receiving medical records for a plurality of patients previously discharged from at least one healthcare facility; parsing the medical records to identify a diagnosis and a length of stay of each of the plurality of patients at the at least one healthcare facility; generate training data based on the diagnosis and the length of stay of each of the plurality of patients at the at least one healthcare facility; and training the ML model using the training data.

Clause 18: A system, comprising: a processor; and memory storing code which, when executed by the processor, performs an operation, the operation comprising: parsing a medical record for a patient to identify an input to a rate calculator; determining, using the rate calculator, a reimbursement or cost rate of the patient at a healthcare facility based on the identified input; predicting, using a machine learning (ML) model, a length of stay of the patient based on a diagnosis of the patient; and determining, before the patient is admitted into the healthcare facility, a revenue stream corresponding to the patient based on the reimbursement or cost rate and the predicted length of stay.

Clause 19: In addition to the clause 18, wherein the operation further comprises: determining, after parsing the medical record, that a required input to the rate calculator is missing; transmitting for display a graphical user interface (GUI) indicating the required input is missing, the GUI display a first field by which a user can provide the required input; and receiving the required input via the GUI, wherein the reimbursement or cost rate is determined after receiving the required input.

Clause 20: In addition to the clause 19, wherein the GUI comprises (i) a second field that is automatically populated to include the identified input and (ii) a selectable element permitting the user to provide an additional input for the rate calculator using a third field.

Clause 21: In addition to the clause 20, wherein the operation further comprises, after determining the reimbursement or cost rate: transmitting for display a second GUI containing the first field, the second field, and the reimbursement or cost rate, wherein the reimbursement or cost rate is calculated using information in the first and second fields, wherein the information comprises at least one of a diagnosis or medication corresponding to the patient.

Clause 22: In addition to the clause 18, 19, 20, or 21, wherein the operation further comprises, before predicting the length of stay: receiving medical records for a plurality of patients previously discharged from at least one healthcare facility; parsing the medical records to identify a diagnosis and a length of stay of each of the plurality of patients at the at least one healthcare facility; generate training data based on the diagnosis and the length of stay of each of the plurality of patients at the at least one healthcare facility; and training the ML model using the training data.

What is claimed is:

1. A method, comprising:

collecting medical records of a plurality of patients previously discharged from one or more healthcare facilities;

generating training data by parsing the medical records to identify, for each patient, a plurality of diagnostic parameters and a corresponding observed length of stay;

grouping the training data into separate groups based on a set of geographic regions associated with the plurality of patients;

training a plurality of neural network (NN) models, each respective NN model of the plurality of NN models corresponding to a respective geographic region of the set of geographic regions and trained based on a respective group of the separate groups, comprising:

for each respective group:

using, as input features, the plurality of diagnostic parameters extracted from the medical records corresponding to the respective group, using, as a labeled output target, the observed length of stay corresponding to each patient of the respective group, and adjusting one or more model parameters of a respective NN model of the plurality of NN models using supervised learning based on using the observed length of stay as a supervisory signal for the respective NN model, wherein the respective NN model learns to generate more accurate predictions for the respective geographic region, as compared to a model trained on non-segmented training data;

receiving a medical record of a current patient;

processing the medical record of the current patient using an optical character recognition (OCR) to convert the medical record into a computer-readable form;

selecting, based on a geographic region associated with the current patient, one of the trained NN models corresponding to a matching group of the separate groups;

parsing, using natural language processing enabled by one or more computer processors, the converted medical record for the current patient to identify an input to a rate calculator and a plurality of diagnostic parameters corresponding to the current patient, comprising:

accessing a database of known medical diagnoses and corresponding diagnosis codes:

determining, using the natural language processing, that the converted medical record does not include a first medical diagnosis included in the database;

determining, using the natural language processing, that the converted medical record includes a derivative of the first medical diagnosis, comprising processing the converted medical record using a machine learning model trained to recognize derivatives of medical diagnoses; and in response to determining that the converted medical record includes the derivative, generating the identified input to the rate calculator;

determining while parsing the converted medical record, a failure in the natural language processing to identify a required input to the rate calculator;

transmitting for display a graphical user interface (GUI) indicating the required input is missing, the GUI displaying a first field by which a user can provide the required input; and receiving the required input via the GUI, wherein the GUI comprises (i) a second field that is automatically populated to include the identified input based on the success of the natural language processing, (ii) a selectable element permitting the user to provide an additional input for the rate calculator using a third field, and (iii) a prompt indicating a value must be entered into the selectable element before a reimbursement or cost rate of the patient at a healthcare facility can be calculated;

determining, using the rate calculator and after receiving the required input, the reimbursement or cost rate of the current patient at a healthcare facility based on the identified input;

predicting, using the selected NN model, a length of stay of the patient based on the plurality of diagnostic parameters corresponding to the current patient;

determining, before the patient is admitted into the healthcare facility, a revenue stream corresponding to the current patient based on the reimbursement or cost rate and the predicted length of stay; and transmitting for display, via the GUI, at least one of the predicted length of stay, the reimbursement or cost rate, or the revenue stream corresponding to the current patient.

2. The method of claim 1, further comprising, after determining the reimbursement or cost rate:

transmitting for display a second GUI containing the first field, the second field, and the reimbursement or cost rate, wherein the reimbursement or cost rate is calculated using information in the first and second fields, wherein the information comprises at least one of a diagnosis or medication corresponding to the patient.

3. The method of claim 1, further comprising, before predicting the length of stay:

parsing the medical record for the current patient to identify the plurality of diagnostic parameters corresponding to the current patient to use as an input to the selected NN model.

4. The method of claim 3, further comprising, before predicting the length of stay:

parsing the medical record for the current patient to identify supplemental information to use as an input to the selected NN model to predict the length of stay, the supplemental information comprising at least one an age or weight of the patient.

5. The method of claim 1, further comprising:

segmenting the training data into groups based on a geographic region associated with each patient; and training, for each group and using a selected training algorithm, a separate NN model configured to predict a length of stay based on the diagnostic parameters.

6. The method of claim 5, wherein generating the training data by parsing medical records of the plurality of patients previously discharged from one or more healthcare facilities comprises:

parsing the medical records to identify supplemental information of each of the plurality of patients, the supplemental information comprising at least one of an age or weight of each of the plurality of patients; and training the selected NN model using the age or weight of each of the plurality of patients.

7. The method of claim 5, further comprising displaying, via the GUI, a confidence score associated with the predicted length of stay corresponding to the current patient.

8. A non-transitory computer readable medium comprising instructions to be executed in a processor, the instructions when executed in the processor perform an operation, the operation comprising:

collecting medical records of a plurality of patients previously discharged from one or more healthcare facilities;

generating training data by parsing the medical records to identify, for each patient, a plurality of diagnostic parameters and a corresponding observed length of stay;

grouping the training data into separate groups based on a set of geographic regions associated with the plurality of patients;

training a plurality of neural network (NN) models, each respective NN model of the plurality of NN models corresponding to a respective geographic region of the set of geographic regions and trained based on a respective group of the separate groups, comprising:

for each respective group:

using, as input features, the plurality of diagnostic parameters extracted from the medical records corresponding to the respective group, using, as a labeled output target, the observed length of stay corresponding to each patient of the respective group, and adjusting one or more model parameters of a respective NN model of the plurality of NN models using supervised learning based on using the observed length of stay as a supervisory signal for the respective NN model, wherein the respective NN model learns to generate more accurate predictions for the respective geographic region, as compared to a model trained on non-segmented training data;

receiving a medical record of a current patient;

processing the medical record of the current patient using an optical character recognition (OCR) to convert the medical record into a computer-readable form:

selecting, based on a geographic region associated with the current patient, one of the trained NN models corresponding to a matching group of the separate groups;

parsing, using natural language processing enabled by one or more computer processors, the converted medical record for the current patient to identify an input to a rate calculator and a plurality of diagnostic parameters corresponding to the current patient, comprising:

accessing a database of known medical diagnoses and corresponding diagnosis codes;

determining, using the natural language processing, that the converted medical record does not include a first medical diagnosis included in the database;

determining, using the natural language processing, that the converted medical record includes a derivative of the first medical diagnosis, comprising processing the converted medical record using a machine learning model trained to recognize derivatives of medical diagnoses; and in response to determining that the converted medical record includes the derivative, generating the identified input to the rate calculator;

determining while parsing the converted medical record, a failure in the natural language processing to identify a required input to the rate calculator;

transmitting for display a GUI indicating the required input is missing, the GUI displaying a first field by which a user can provide the required input; and receiving the required input via the GUI, wherein the GUI comprises (i) a second field that is automatically populated to include the identified input based on the success of the natural language processing, (ii) a selectable element permitting the user to provide an additional input for the rate calculator using a third field, and (iii) a prompt indicating a value must be entered into the selectable element before a reimbursement or cost rate of the patient at a healthcare facility can be calculated;

determining, using the rate calculator and after receiving the required input, the reimbursement or cost rate of the current patient at a healthcare facility based on the identified input;

predicting, using the selected NN model, a length of stay of the patient based on the plurality of diagnostic parameters corresponding to the current patient;

determining, before the patient is admitted into the healthcare facility, a revenue stream corresponding to the current patient based on the reimbursement or cost rate and the predicted length of stay; and transmitting for display, via the GUI, at least one of the predicted length of stay, the reimbursement or cost rate, or the revenue stream corresponding to the current patient.

9. The non-transitory computer readable medium of claim 8, wherein the operation further comprises, after determining the reimbursement or cost rate:

transmitting for display a second GUI containing the first field, the second field, and the reimbursement or cost rate, wherein the reimbursement or cost rate is calculated using information in the first and second fields, wherein the information comprises at least one of a diagnosis or medication corresponding to the patient.

10. The non-transitory computer readable medium of claim 8, wherein the operation further comprises, before predicting the length of stay:

parsing the medical record for the current patient to identify the plurality of diagnostic parameters corresponding to the current patient to use as an input to the selected NN model.

11. The non-transitory computer readable medium of claim 10, wherein the operation further comprises, before predicting the length of stay:

parsing the medical record for the current patient to identify supplemental information to use as an input to the selected NN model to predict the length of stay, the supplemental information comprising at least one an age or weight of the patient.

12. The non-transitory computer readable medium of claim 8, wherein the operation further comprises:

segmenting the training data into groups based on a geographic region associated with each patient; and training, for each group and using a selected training algorithm, a separate NN model configured to predict a length of stay based on the diagnostic parameters.

13. A system, comprising:

a processor; and memory storing code which, when executed by the processor, performs an operation, the operation comprising:

collecting medical records of a plurality of patients previously discharged from one or more healthcare facilities;

generating training data by parsing the medical records to identify, for each patient, a plurality of diagnostic parameters and a corresponding observed length of stay;

grouping the training data into separate groups based on a set of geographic regions associated with the plurality of patients;

training a plurality of neural network (NN) models, each respective NN model of the plurality of NN models corresponding to a respective geographic region of the set of geographic regions and trained based on a respective group of the separate groups, comprising:

for each respective group:

using, as input features, the plurality of diagnostic parameters extracted from the medical records corresponding to the respective group, using, as a labeled output target, the observed length of stay corresponding to each patient of the respective group, and adjusting one or more model parameters of a respective NN model of the plurality of NN models using supervised learning based on using the observed length of stay as a supervisory signal for the respective NN model, wherein the respective NN model learns to generate more accurate predictions for the respective geographic region, as compared to a model trained on non-segmented training data;

receiving a medical record of a current patient;

processing the medical record of the current patient using an optical character recognition (OCR) to convert the medical record into a computer-readable form;

selecting, based on a geographic region associated with the current patient, one of the trained NN models corresponding to a matching group of the separate groups;

parsing, using natural language processing enabled by one or more computer processors, the converted medical record for the current patient to identify an input to a rate calculator and a plurality of diagnostic parameters corresponding to the current patient, comprising:

accessing a database of known medical diagnoses and corresponding diagnosis codes;

determining, using the natural language processing, that the converted medical record does not include a first medical diagnosis included in the database;

determining, using the natural language processing, that the converted medical record includes a derivative of the first medical diagnosis, comprising processing the converted medical record using a machine learning model trained to recognize derivatives of medical diagnoses; and in response to determining that the converted medical record includes the derivative, generating the identified input to the rate calculator;

determining while parsing the converted medical record, a failure in the natural language processing to identify a required input to the rate calculator;

transmitting for display a GUI indicating the required input is missing, the GUI displaying a first field by which a user can provide the required input;

receiving the required input via the GUI, wherein the GUI comprises (i) a second field that is automatically populated to include the identified input based on success of the natural language processing, (ii) a selectable element permitting the user to provide an additional input for the rate calculator using a third field, and (iii) a prompt indicating a value must be entered into the selectable element before a reimbursement or cost rate of the patient at a healthcare facility can be calculated;

determining, using the rate calculator and after receiving the required input, the reimbursement or cost rate of the current patient at a healthcare facility based on the identified input;

predicting, using the selected NN model, a length of stay of the patient based on the plurality of diagnostic parameters corresponding to the current patient;

determining, before the patient is admitted into the healthcare facility, a revenue stream corresponding to the current patient based on the reimbursement or cost rate and the predicted length of stay; and transmitting for display, via the GUI, at least one of the predicted length of stay, the reimbursement or cost rate, or the revenue stream corresponding to the current patient.

14. The system of claim 13, wherein the operation further comprises, after determining the reimbursement or cost rate:

transmitting for display a second GUI containing the first field, the second field, and the reimbursement or cost rate, wherein the reimbursement or cost rate is calculated using information in the first and second fields, wherein the information comprises at least one of a diagnosis or medication corresponding to the patient.

15. The system of claim 13, wherein the operation further comprises:

segmenting the training data into groups based on a geographic region associated with each patient; and training, for each group and using a selected training algorithm, a separate NN model configured to predict a length of stay based on the diagnostic parameters.

16. The method of claim 1, wherein parsing the medical record of the current patient comprises:

pre-processing the medical records by:

tokenizing text in the medical records, normalizing the tokenized text, and converting the tokenized text into an object that is represented numerically using at least one of one-hot encodings or word embedding vectors.

17. The non-transitory computer readable medium of claim 8, wherein parsing the medical record of the current patient comprises:

pre-processing the medical records by:

tokenizing text in the medical records, normalizing the tokenized text, and converting the tokenized text into an object that is represented numerically using at least one of one-hot encodings or word embedding vectors.

18. The system of claim 13, wherein parsing the medical record of the current patient comprises:

pre-processing the medical records by:

tokenizing text in the medical records, normalizing the tokenized text, and converting the tokenized text into an object that is represented numerically using at least one of one-hot encodings or word embedding vectors.

* * * * *